(12) United States Patent
Shioda

(10) Patent No.: US 10,849,484 B2
(45) Date of Patent: Dec. 1, 2020

(54) MEDICAL OBSERVATION APPARATUS

(71) Applicant: Sony Olympus Medical Solutions Inc., Tokyo (JP)

(72) Inventor: Keiji Shioda, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 16/274,308

(22) Filed: Feb. 13, 2019

(65) Prior Publication Data

US 2019/0290101 A1 Sep. 26, 2019

(30) Foreign Application Priority Data

Mar. 23, 2018 (JP) ................. 2018-055790

(51) Int. Cl.
| | | |
|---|---|---|
| *A61B 1/04* | (2006.01) | |
| *A61B 1/00* | (2006.01) | |
| *G02B 21/00* | (2006.01) | |
| *A61B 90/30* | (2016.01) | |
| *A61B 90/50* | (2016.01) | |
| *A61B 1/06* | (2006.01) | |
| *A61B 90/00* | (2016.01) | |

(52) U.S. Cl.
CPC ...... *A61B 1/00045* (2013.01); *A61B 1/00193* (2013.01); *A61B 1/04* (2013.01); *A61B 90/30* (2016.02); *G02B 21/0012* (2013.01); *A61B 1/00009* (2013.01); *A61B 1/0638* (2013.01); *A61B 1/0646* (2013.01); *A61B 1/0661* (2013.01); *A61B 90/361* (2016.02); *A61B 90/37* (2016.02); *A61B 2090/502* (2016.02)

(58) Field of Classification Search
None
See application file for complete search history.

(56) References Cited

U.S. PATENT DOCUMENTS

2005/0206583 A1* 9/2005 Lemelson ............ A61B 5/7445 345/7
2010/0283842 A1* 11/2010 Guissin ................. G02B 13/06 348/68

FOREIGN PATENT DOCUMENTS

JP 2003-204972 7/2003

* cited by examiner

*Primary Examiner* — Christopher G Findley
(74) *Attorney, Agent, or Firm* — Xsensus LLP

(57) ABSTRACT

There is provided a wearable medical observation apparatus used by being worn on a head of a user, including: a first observation section having a configuration enabling a first observation of an observation target through an optical system including at least an objective lens; a second observation section having a configuration enabling a second observation of an observation target by a first medical observation image in which the observation target is imaged by a first imaging device; and a control section configured to control an observation state of the observation target.

19 Claims, 6 Drawing Sheets

MEDICAL OBSERVATION APPARATUS

CROSS REFERENCE TO RELATED APPLICATIONS

This application claims the benefit of Japanese Priority Patent Application JP 2018-055790 filed Mar. 23, 2018, the entire contents of which are incorporated herein by reference.

BACKGROUND

The present disclosure relates to a medical observation apparatus.

Recently, in the medical field, to perform microsurgery such as neurosurgical procedures, or to perform an abdominal or open chest surgery or the like, for example, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" in some cases. Also, in the following, a captured image (a moving image or a still image; the same applies hereinafter) in which an observation target is captured by an imaging device is denoted a "medical captured image".

Examples of optical medical observation apparatus include an optical magnifying glass for observing at a relatively low magnification, an optical surgical microscope for observing at a higher magnification than an optical magnifying glass, and the like. An optical magnifying glass is worn on the head of a user such as a surgeon who uses the optical medical observation apparatus, and is used by having the user peer into an eyepiece lens included in the optical magnifying glass, for example.

With an electronic imaging medical observation apparatus, along with the increased image quality of imaging devices, the increased image quality of display apparatus on which captured images are displayed, and the like, the same or higher image quality than an optical surgical microscope has come to be obtained. Also, it is possible for a user who uses an electronic imaging medical observation apparatus (for example, medical personnel such as a surgeon or a surgeon's assistant) to move the position of the imaging device more freely. For this reason, using an electronic imaging medical observation apparatus has an advantage of enabling more flexible support of microsurgery, and in the medical field, utilization of electronic imaging medical observation apparatus is progressing.

Among these, technologies related to optical magnifying glasses are being developed. Technologies in which an illuminating device and an imaging device are built into an optical magnifying glass and an image captured by the imaging device is transmitted wirelessly include the technology described in JP 2003-204972A, for example.

SUMMARY

As described above, an optical magnifying glass is a medical observation apparatus for observing at a low magnification compared to a surgical microscope. Even in abdominal or open chest surgeries that often have been performed with the naked eye or an optical magnifying glass in the past, situations demanding high magnification to perform less invasive surgery are increasing, and there is an increasing need to use a surgical microscope temporarily. However, the idea of observing by switching between the function of an optical magnifying glass and the function of a surgical microscope has not been proposed. Also, if the magnification of a surgical microscope is lowered unnecessarily, there is a risk of making the medical observation apparatus bulkier, whereas if the magnification of an optical magnifying glass is raised, even slight head shaking causes the picture to become blurry, and risks making the optical magnifying glass difficult to use.

The present disclosure proposes a novel and improved medical observation apparatus capable of including both the function of an optical magnifying glass and the function of a surgical microscope.

According to an embodiment of the present disclosure, there is provided a wearable medical observation apparatus used by being worn on a head of a user, including: a first observation section having a configuration enabling a first observation of an observation target through an optical system including at least an objective lens; a second observation section having a configuration enabling a second observation of an observation target by a first medical observation image in which the observation target is imaged by a first imaging device; and a control section configured to control an observation state of the observation target.

According to an embodiment of the present disclosure, a medical observation apparatus including both the function of an optical magnifying glass and the function of a surgical microscope is realized.

Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
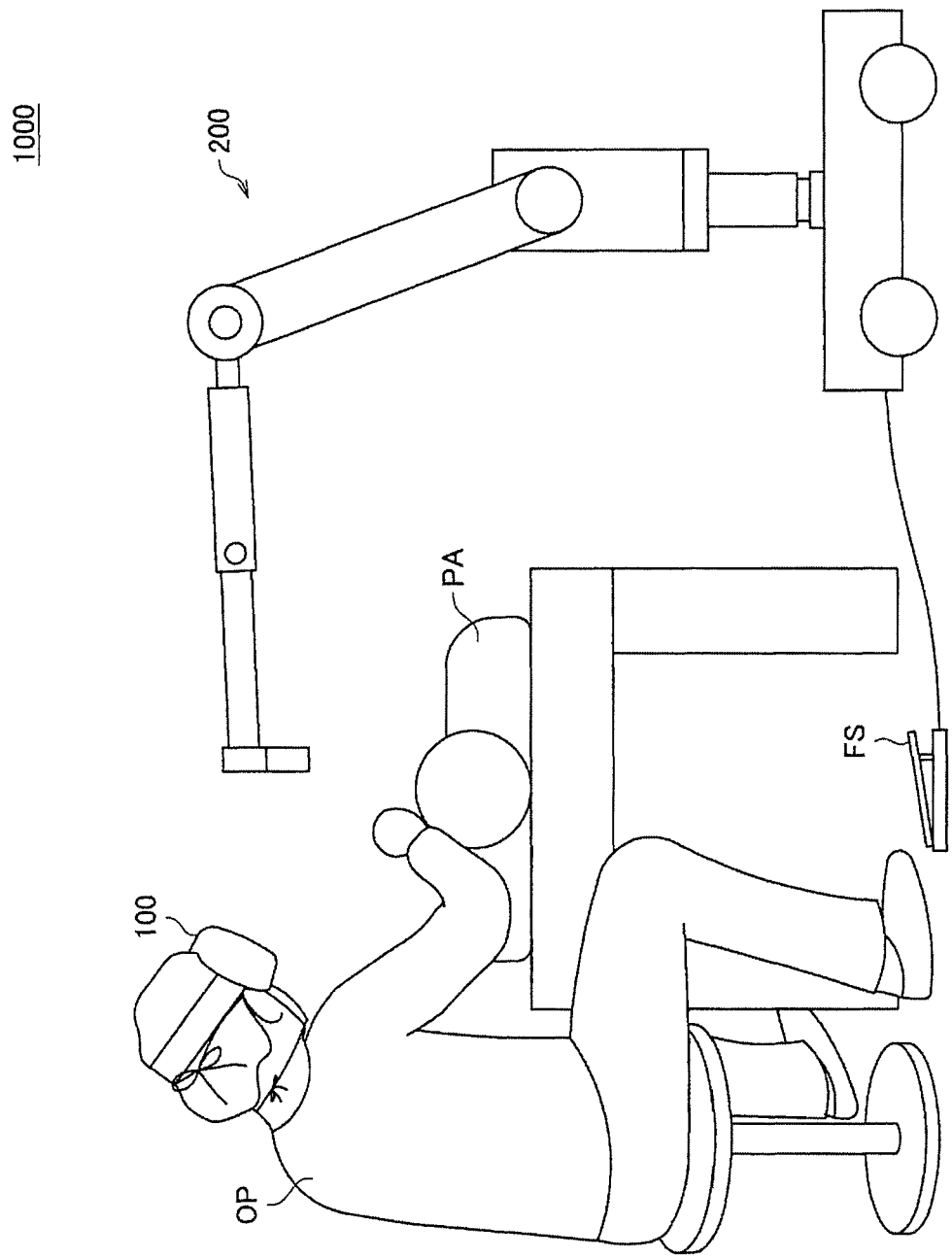
FIG. 1 is an explanatory diagram illustrating one example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.
1. Medical observation system according to present embodiment
    [1] Configuration of medical observation system
    [1-1] Electronic imaging medical observation apparatus
    [1-2] Medical observation apparatus according to present embodiment
    [2] Example of advantageous effects exhibited by use of medical observation apparatus according to present embodiment (Medical Observation System According to Present Embodiment)

Hereinafter, one example of the medical observation system according to the present embodiment will be described.

[1] Configuration of Medical Observation System

FIG. 1 is an explanatory diagram illustrating one example of the configuration of a medical observation system 1000 according to the present embodiment. The medical observation system 1000 illustrated in FIG. 1 includes a medical observation apparatus 100 and a medical observation apparatus 200, for example.

The medical observation apparatus 100 is a wearable medical observation apparatus that is used by being worn on the head of a user. FIG. 1 illustrates an example in which the medical observation apparatus 100 is worn directly on the head of a surgeon OP (one example of the user of the medical observation apparatus 100), but an example of the medical observation apparatus 100 is not limited to the example illustrated in FIG. 1. For example, the medical observation apparatus 100 may also be worn indirectly on the head of the surgeon OP by being used as a pair of glasses that the surgeon OP wears on one's head.

Also, the medical observation apparatus 100 is a medical observation apparatus that includes both the function of an optical magnifying glass and the function of a surgical microscope. The medical observation apparatus 100 includes the function of an optical magnifying glass by being provided with a "configuration enabling the observation of an observation target through an optical system that at least includes an objective lens" described later. Also, the medical observation apparatus 100 includes the function of a surgical microscope by being provided with a "configuration enabling the observation of a medical observation image captured by an imaging device provided in an electronic imaging medical observation apparatus" described later.

In the following, observation of the observation target through the optical system above is designated the "first observation". Also, in the following, observation of a medical observation image captured by an imaging device provided in the electronic imaging medical observation apparatus is designated the "second observation". Herein, the first observation is observation by the function of an optical magnifying glass, and corresponds to magnifying glass observation at a relatively low magnification. Also, the second observation is observation by the function of a surgical microscope, and corresponds to surgical microscope observation at a medium-high magnification. In other words, the observation magnification of the observation target in the first observation is lower than the observation magnification of the observation target in the second observation.

In the following, a medical observation image related to the second observation is designated the "first medical observation image", and an imaging device related to the second observation (in other words, the imaging device provided in the electronic imaging medical observation apparatus that captures the first medical observation image) is designated the "first imaging device".

As described later, the first observation according to the present embodiment includes "optical observation in which the user observes the observation target directly through the optical system" and "observation in which the user observes the observation target by a medical observation image captured by the imaging device that images the observation target through the optical system". In the following, a medical observation image related to the first observation is designated the "second medical observation image", and an imaging device related to the first observation (in other words, the imaging device that captures the second medical observation image and images the observation target through the optical system) is designated the "second imaging device".

The medical observation apparatus 200 is an electronic imaging medical observation apparatus.

By an imaging device (described later) provided in the medical observation apparatus 200, an observation target patient PA (a patient who undergoes a medical procedure) is captured. The captured image that captures the above patient who undergoes a medical procedure corresponds to one example of a medical captured image. The imaging device (described later) provided in the medical observation apparatus 200 corresponds to one example of an imaging device external to the medical observation apparatus 100.

The medical captured image captured in the medical observation apparatus 200 may be displayed on a display screen of a display device (described later) provided in the medical observation apparatus 100, for example.

The surgeon OP is able to perform a medical procedure on the patient PA by the first observation realized by the function of an optical magnifying glass. Additionally, the surgeon OP is also able to perform a medical procedure on the patient PA while looking at a medical captured image displayed on the display screen of the display device (described later). In other words, the surgeon OP who uses the medical observation apparatus 100 performs a medical procedure on the patient PA through the first observation or the second observation of the observation target.

The medical observation image in which the observation target is imaged by the imaging device (described later) provided in the medical observation apparatus 200 corresponds to one example of the "first medical observation image". Also, observation of the medical observation image in which the observation target is imaged by the imaging device (described later) provided in the medical observation apparatus 200 corresponds to one example of the "second observation".

The surgeon OP is able to switch between performing the first observation of the observation target using the medical observation apparatus 100 or performing the second observation using the medical observation apparatus 100 by operating an "operating device (described later) external to the medical observation apparatus 200, such as a footswitch FS or an operating device provided in the medical observation apparatus 200" or an "operating device provided in the medical observation apparatus 100", for example.

Also, the surgeon OP operates an operating device external to the medical observation apparatus 200, such as a footswitch FS, or an operating device (described later) provided in the medical observation apparatus 200, thereby causing an arm (described later) and the imaging device (described later) provided in the medical observation apparatus 200 to operate, and putting the medical observation apparatus 200 into a desired state.

Note that the medical observation system according to the present embodiment is not limited to the example illustrated in FIG. 1.

For example, the medical observation system according to the present embodiment additionally may include a medical control apparatus (not illustrated) that controls various operations in the medical observation apparatus 200. The medical control apparatus (not illustrated) may be, for example, a "medical controller", a "computer such as a tablet", or the like. Also, the medical control apparatus (not illustrated) may be, for example, an integrated circuit (IC) that can be embedded in equipment like the above.

Also, the medical observation system according to the present embodiment additionally may include a navigation apparatus, for example. The navigation apparatus is driven with power supplied from an internal power source, such as a battery provided in the navigation apparatus, or with power supplied from a connected external power source, for example.

The navigation apparatus is a piece of medical equipment for realizing what is called a medical navigation system. For example, the navigation apparatus detects the spatial position of a position-detecting probe, and causes an image corresponding to the detected spatial position to be displayed on the display screen of any display device.

In the case in which a medical navigation system is realized by a navigation apparatus, for example, a medical personnel member moves the position-detecting probe to a position corresponding to the surgical site. In this case, the position corresponding to the surgical site is detected. Also, in the case in which a medical navigation system is realized by a navigation apparatus, the position-detecting probe may be provided in any of various apparatus such as the medical observation apparatus 100 or the medical observation apparatus 200, for example. In this case, the position of the various apparatus is detected. The position-detecting probe may be a dedicated instrument or an adapter-style device that is attached to a medical instrument, the medical observation apparatus 100, or the like. Additionally, the position-detecting probe may also be realized by a method of indicating the position virtually from the direction and observation distance at which the medical observation apparatus 100 is observing. By detecting the spatial position of the position-detecting probe by any position-detecting method, such as an optical position-detecting method utilizing infrared rays or the like or a magnetic field position-detecting method, the navigation apparatus detects the position of the surgical site in the patient or the position of various apparatus. The position sensor that detects the spatial position of the position-detecting probe may be provided in the navigation apparatus or provided at any position external to the navigation apparatus, for example. For example, in the case of detecting the position of the surgical site in the patient, a medical personnel member such as the surgeon OP looks at an image corresponding to the detected spatial position displayed on the display screen, and thereby is able to visually recognize which part of the patient corresponds to the part being treated.

The navigation apparatus may also include a function of transmitting position information indicating the detected spatial position of the position-detecting probe to an external apparatus such as the medical observation apparatus 100 or the electronic imaging medical observation apparatus 200. Position information corresponding to the medical observation apparatus 100 fulfills the role of information indicating the position of the first observation, for example.

For example, by transmitting position information corresponding to the medical observation apparatus 100 and position information corresponding to the electronic imaging medical observation apparatus 200 to the electronic imaging medical observation apparatus 200, in the medical observation apparatus 200, it is also possible to control the arm (described later) such that an image is captured from a position corresponding to the "position indicated by the position information corresponding to the medical observation apparatus 100". Also, for example, by controlling the arm (described later) such that an image is captured from a position corresponding to the "position indicated by the position information corresponding to the medical observation apparatus 100" in the medical observation apparatus 200, it becomes possible to align the observation field of view of the first observation realized by the function of an optical magnifying glass and the observation field of view of the second observation (that is, the observation field of view of the observation of the first medical observation image) in the medical observation apparatus 100.

Also, for example, by transmitting position information corresponding to the medical observation apparatus 100 and position information corresponding to the electronic imaging medical observation apparatus 200 to the medical observation apparatus 100, in the medical observation apparatus 100, it becomes possible to present the position of the observation field of view of the second observation inside the observation field of view of the first observation. An example of presenting the position of the observation field of view of the second observation inside the observation field of view of the first observation will be described later.

Hereinafter, one example of the configuration of each apparatus included in the medical observation system 1000 according to the first example illustrated in FIG. 1 will be described.

[1-1] Electronic Imaging Medical Observation Apparatus

Figure 2:
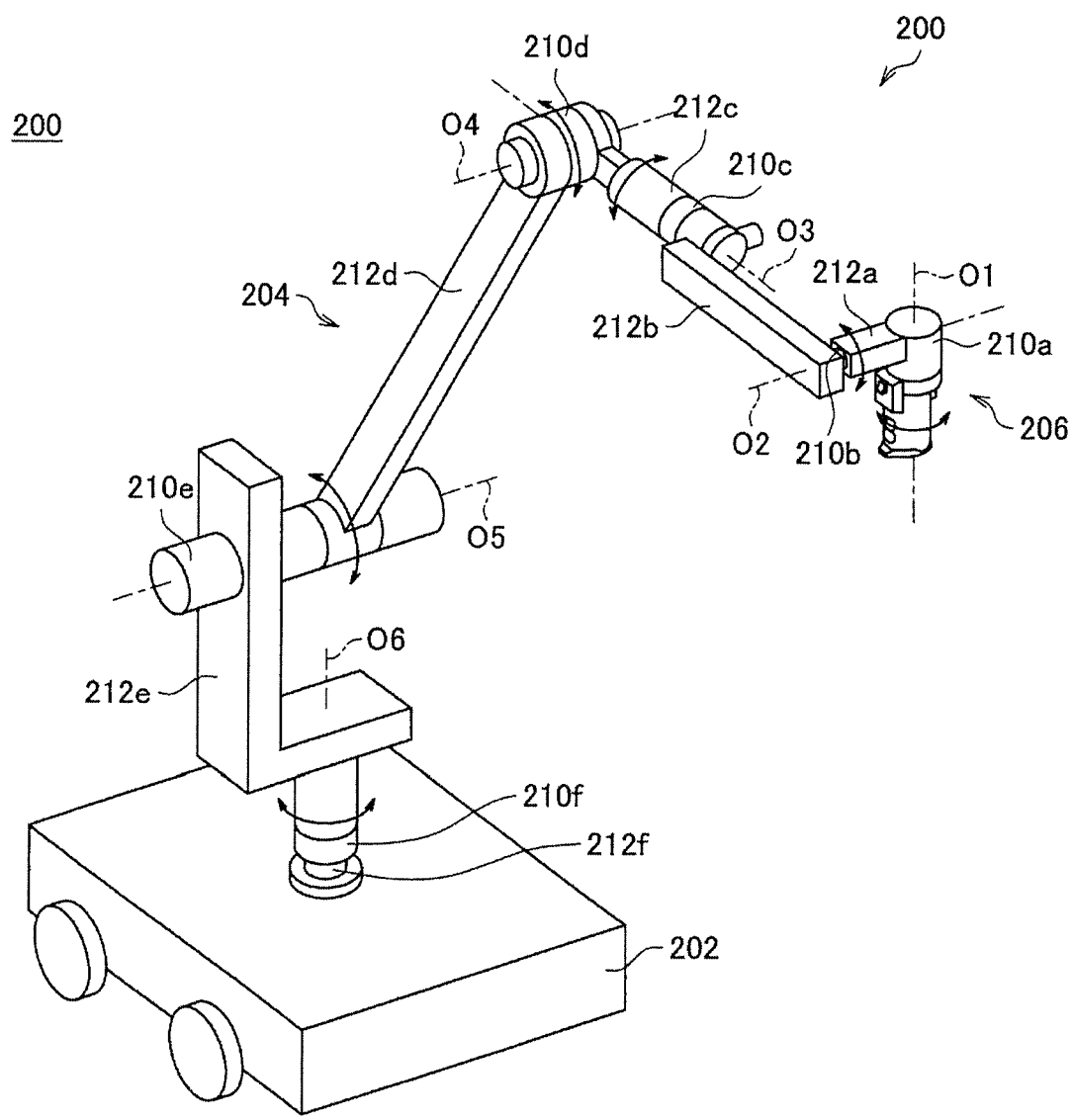
FIG. 2 is an explanatory diagram illustrating one example of the configuration of an electronic imaging medical observation apparatus included in a medical observation system according to the present embodiment.

FIG. 2 is an explanatory diagram illustrating one example of the configuration of the electronic imaging medical observation apparatus 200 included in the medical observation system 1000 according to the present embodiment.

The medical observation apparatus 200 is provided with a base 202, an arm 204, and an imaging device 206, for example.

Additionally, although not illustrated in FIG. 2, the medical observation apparatus 200 may also be provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The medical observation apparatus 200 runs on electric power supplied from an internal power source such as a battery provided in the medical observation apparatus 200, on electric power supplied from a connected external power source, or the like, for example.

The one or multiple processors (not illustrated) function as the control section in the medical observation apparatus 200. The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) functions as a storage section (not illustrated) in the medical observation apparatus 200. A variety of data is stored on the recording medium (not illustrated), including various applications, for example. Herein, examples of the recording medium (not illustrated) include a magnetic recording medium such as a hard disk, non-volatile memory such as flash memory, and the like. Additionally, the recording medium (not illustrated) may also be removable from the medical observation apparatus 200.

The communication device (not illustrated) is a communication device provided in the medical observation apparatus 200, and fulfills a role of communicating in a wireless or wired manner with an external apparatus such as the medical observation apparatus 100. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a RF circuit (wireless communication), a LAN terminal and a transmitting-receiving circuit (wired communication), and the like.

[1-1-1] Base 202

The base 202 is the base of the medical observation apparatus 200. One end of the arm 204 is connected to the base 202, and the base 202 supports the arm 204 and the imaging device 206.

Also, casters are provided on the base 202, for example, and the medical observation apparatus 200 contacts the floor through the casters. By providing the casters, the medical observation apparatus 200 is able to move easily over the floor by the casters.

[1-1-2] Arm 204

The arm 204 includes multiple links joined to each other by joint sections. In addition, the arm 204 supports the imaging device 206. The imaging device 206 supported by the arm 204 is movable three-dimensionally, and after moving, the position and the attitude of the imaging device 206 are maintained by the arm 204.

More specifically, the arm 204 includes, for example, multiple joint sections 210a, 210b, 210c, 210d, 210e, and 210f, and multiple links 212a, 212b, 212c, 212d, 212e, and 212f rotatably joined to each other by the joint sections 210a, 210b, 210c, 210d, 210e, and 210f. The rotatable range of each of the joint sections 210a, 210b, 210c, 210d, 210e, and 210f is set arbitrarily during the design stage, the manufacturing stage, or the like so that the desired motion of the arm 204 is realized.

In other words, in the medical observation apparatus 200 illustrated in FIG. 2, six degrees of freedom are realized in relation to the movement of the imaging device 206 by six rotation axes (first axis O1, second axis O2, third axis O3, fourth axis O4, fifth axis O5, and sixth axis O6) corresponding to the six joint sections 210a, 210b, 210c, 210d, 210e, and 210f included in the arm 204. More specifically, in the medical observation apparatus 200 illustrated in FIG. 2, motion with six degrees of freedom, including three degrees of translational freedom and three degrees of rotational freedom, is realized.

Actuators (not illustrated) are provided in each of the joint sections 210a, 210b, 210c, 210d, 210e, and 210f. Each of the joint sections 210a, 210b, 210c, 210d, 210e, and 210f rotates about the corresponding rotation axis by the driving of the actuators (not illustrated). The driving of the actuators (not illustrated) is controlled by, for example, a processor provided in the medical observation apparatus 200, or an external medical control apparatus (not illustrated).

Each of the joint sections 210a, 210b, 210c, 210d, 210e, and 210f may be provided with angle sensors (not illustrated) capable of detecting a rotational angle for each of six rotation axes. The angle sensors may be, for example, rotary encoders, or any sensors capable of obtaining a rotational angle for each of six rotation axes, such as angular velocity sensors.

By having each of the joint sections 210a, 210b, 210c, 210d, 210e, 210f rotate about the corresponding rotation axis by the driving of the actuators (not illustrated), various operations of the arm 204, such as extending and contracting (folding up) the arm 204, for example, are realized.

The joint section 210a has an approximately cylindrical shape, and supports the imaging device 206 (the top end of the imaging device 206 in FIG. 2) on the front end portion of the joint section 210a (the bottom end portion in FIG. 2), so as to allow revolution about a rotation axis (first axis O1) parallel to the central axis of the imaging device 206. Herein, the medical observation apparatus 200 is configured so that the first axis O1 is aligned with the optical axis in the imaging device 206. In other words, by causing the imaging device 206 to revolve about the first axis O1 illustrated in FIG. 2, the medical captured image captured by the imaging device 206 becomes an image which has changed so that the field of view rotates.

The link 212a is an approximately rod-shaped member, and securely supports the joint section 210a. The link 212a extends in a direction orthogonal to the first axis O1, for example, and is connected to the joint section 210b.

The joint section 210b has an approximately cylindrical shape, and supports the link 212a so as to allow revolution about a rotation axis (second axis O2) orthogonal to the first axis O1. Also, the link 212b is securely connected to the joint section 210b.

The link 212b is an approximately rod-shaped member, and extends in a direction orthogonal to the second axis O2. Also, each of the joint section 210b and the joint section 210c is connected to the link 212b.

The joint section 210c has an approximately cylindrical shape, and supports the link 212b so as to allow revolution about a rotation axis (third axis O3) mutually orthogonal to each of the first axis O1 and the second axis O2. Also, one end of the link 212c is securely connected to the joint section 210c.

Herein, by having the front end side (the side on which the imaging device 206 is provided) of the arm 204 revolve about the second axis O2 and the third axis O3, the imaging device 206 can be made to move so that the position of the imaging device 206 in the horizontal plane is changed. In other words, in the medical observation apparatus 200, controlling the rotation about the second axis O2 and the third axis O3 makes it possible to move the field of view of the medical captured image in a flat plane.

The link 212c is a member in which one end has an approximately cylindrical shape, and the other end has an approximately rod-like shape. On the side of the one end of the link 212c, the joint section 210c is securely connected so that the central axis of the joint section 210c and the central axis of the approximately cylindrical shape are the same. Also, on the side of the other end of the link 212c, the joint section 210d is connected.

The joint section 210d has an approximately cylindrical shape, and supports the link 212c so as to allow revolution about a rotation axis (fourth axis O4) orthogonal to the third axis O3. The link 212d is securely connected to the joint section 210d.

The link 212d is an approximately rod-shaped member, and extends orthogonally to the fourth axis O4. One end of the link 212d is securely connected to the joint section 210d so as to abut the approximately cylindrical side face of the joint section 210d. Also, the joint section 210e is connected to the other end of the link 212d (the end on the opposite side of the side where the joint section 210d is connected).

The joint section 210e has an approximately cylindrical shape, and supports one end of the link 212d so as to allow revolution about a rotation axis (fifth axis O5) parallel to the fourth axis O4. Also, one end of the link 212e is securely connected to the joint section 210e.

Herein, the fourth axis O4 and the fifth axis O5 are rotation axis about which the imaging device 206 may be moved in the vertical direction. By having the front end side (the side on which the imaging device 206 is provided) of the arm 204 revolve about the fourth axis O4 and the fifth axis O5, the position of the imaging device 206 in the vertical direction changes. Thus, by having the front end side (the side on which the imaging device 206 is provided) of the arm 204 revolve about the fourth axis O4 and the fifth axis O5, changing the distance between the imaging device 206 and an observation target, such as an operating site of a patient, becomes possible.

The link 212e is a member that includes a combination of a first member having an approximate L-shape with one edge extending in the vertical direction while the other edge extends in the horizontal direction, and a rod-like second member that extends vertically downward from the part of the first member that extends in the horizontal direction. The joint section 210e is securely connected to the part of the first member of the link 212e that extends in the vertical direction. Also, the joint section 210f is connected to the second member of the link 212e.

The joint section 210f has an approximately cylindrical shape, and supports the link 212e so as to allow revolution about a rotation axis (sixth axis O6) parallel to the vertical direction. Also, the link 212f is securely connected to the joint section 210f.

The link 212f is an approximately rod-shaped member, and extends in the vertical direction. The joint section 210f is connected to one end of the link 212f. Also, the other end of the link 212f (the end on the opposite side of the side where the joint section 210f is connected) is securely connected to the base 202.

By having the arm 204 include the configuration indicated above, in the medical observation apparatus 200, six degrees of freedom are realized with respect to the movement of the imaging device 206.

Note that the configuration of the arm 204 is not limited to the example indicated above.

For example, each of the joint sections 210a, 210b, 210c, 210d, 210e, and 210f of the arm 204 may be provided with a brake that restrains rotation in each of the joint sections 210a, 210b, 210c, 210d, 210e, and 210f. The brake according to the present embodiment may be a brake of an arbitrary method, such as a mechanically driven brake or an electrically driven electromagnetic brake, for example.

The driving of the above brakes is controlled by, for example, a processor provided in the medical observation apparatus 200, or an external medical control apparatus (not illustrated). By controlling the driving of the above brakes, in the medical observation apparatus 200, the operating mode of the arm 204 is set. Examples of operating modes of the arm 204 include a locked mode and a free mode.

Herein, the locked mode according to the present embodiment is, for example, an operating mode in which the position and the attitude of the imaging device 206 are locked by using brakes to restrain rotation about each rotation axis provided in the arm 204. By having the arm 204 enter the locked mode, the operating state of the medical observation apparatus 200 becomes a locked state in which the position and the attitude of the imaging device 206 are locked.

Also, the free mode according to the present embodiment is an operating mode in which the above brakes are released, thereby allowing each rotation axis provided in the arm 204 to rotate freely. For example, in the free mode, the position and the attitude of the imaging device 206 are adjustable by direct operations performed by the surgeon. Herein, a direct operation according to the present embodiment means, for example, an operation in which the surgeon grips the imaging device 206 with his or her hand, and directly moves the imaging device 206.

[1-1-3] Imaging Device 206

The imaging device 206 is supported by the arm 204, and images an observation target such as an operating site of a patient, for example. Imaging in the imaging device 206 is controlled by, for example, a processor provided in the medical observation apparatus 200, or an external medical control apparatus (not illustrated).

The imaging device 206 has a configuration corresponding to an electronic imaging microscope, for example.

Figure 3:
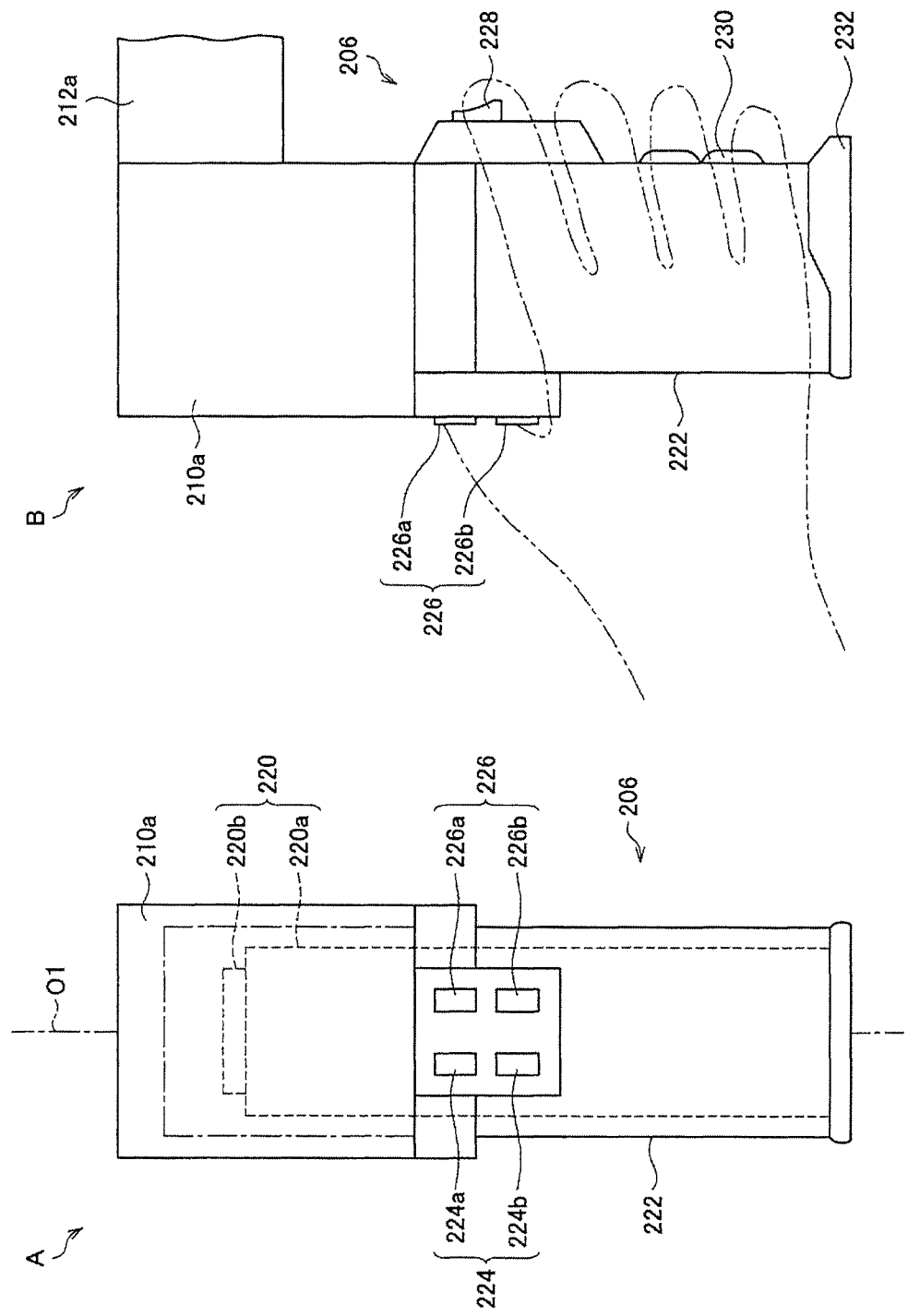
FIG. 3 is an explanatory diagram for explaining one example of the configuration of an imaging device provided in the electronic imaging medical observation apparatus according to the present embodiment.

FIG. 3 is an explanatory diagram for explaining an example of the configuration of the imaging device 206 provided in the electronic imaging medical observation apparatus 200 according to the present embodiment.

For example, the imaging device 206 includes an imaging member 220 and a barrel member 222 having an approximately cylindrical shape, with the imaging member 220 being provided inside the barrel member 222.

On an aperture on the bottom end of the barrel member 222 (the lower end in FIG. 3), for example, a cover glass (not illustrated) for protecting the imaging member 220 is provided.

Additionally, for example, a light source (not illustrated) is provided inside the barrel member 222, and during imaging, the subject is irradiated with illuminating light radiating from the light source through the cover glass. Reflected light (observation light) from the subject irradiated with illuminating light enters the imaging member 220 through the cover glass (not illustrated), whereby an image signal indicating the subject (an image signal indicating a medical captured image) is obtained by the imaging member 220.

As the imaging member 220, any of various known types of configurations used in an electronic imaging microscope section can be applied.

To give one example, the imaging member 220 includes an optical system 220a and an image sensor 220b including an imaging element that takes an image of an observation target with light transmitted through the optical system 220a, for example. The optical system 220a includes optical elements such as a mirror and one or multiple lenses, such as an objective lens, a zoom lens, and a focus lens, for example. Examples of the image sensor 220b include an image sensor using multiple imaging elements, such as a complementary metal-oxide semiconductor (CMOS) or a charge-coupled device (CCD).

The imaging member 220, by including two or more imaging devices provided with an optical system 220a and an image sensor 220b, for example, functions as what is called a stereo camera. In the configuration of the imaging device 206 that functions as a stereo camera, the optical system may be a Galileo optical system or a Greenough optical system.

Each imaging device included in the imaging member 220 is equipped with one or multiple functions typically provided in an electronic imaging microscope section, such as a zoom function (one or both of an optical zoom function and an electronic zoom function) and an autofocus (AF) function.

In addition, the imaging member 220 may also be configured to be capable of imaging at what are called high resolutions, such as 4K and 8K, for example. By configuring the imaging member 220 to be capable of imaging at high resolutions, it becomes possible to ensure a predetermined resolution (such as full HD image quality, for example), while also displaying an image on the display apparatus having a large display screen, such as 50 inches or more, for example. For this reason, visibility is improved for the surgeon watching the display screen. Also, by configuring the imaging member 220 to be capable of imaging at high resolutions, even if the captured image is enlarged by the electronic zoom function and displayed on the display screen of the display apparatus, it is still possible to ensure a predetermined resolution. Furthermore, in the case of using the electronic zoom function to ensure a predetermined resolution, since it is possible to reduce the performance of the optical zoom function in the imaging device 206, the optical system of the imaging device 206 can be simplified, and the imaging device 206 can be configured more compactly.

In the imaging device 206, for example, various operating devices for controlling the operation of the imaging device 206 are provided. For example, in FIG. 3, a zoom switch 224, a focus switch 226, and an operating mode change switch 228 are provided on the imaging device 206. Note that the positions and shapes in which to provide the zoom switch 224, the focus switch 226, and the operating mode change switch 228 obviously are not limited to the example illustrated in FIG. 3.

The zoom switch 224 and the focus switch 226 are an example of an operating device for adjusting the imaging parameters in the imaging device 206.

The zoom switch 224 includes, for example, a zoom-in switch 224a that increases the zoom magnification (enlargement ratio), and a zoom-out switch 224b that decreases the zoom magnification. By performing an operation on the zoom switch 224, the zoom magnification is adjusted, and the zoom is adjusted.

The focus switch 226 includes, for example, a long-range focus switch 226a that increases the focal length to the observation target (subject), and a close-range focus switch 226b that decreases the focal length to the observation target. By performing an operation on the focus switch 226, the focal length is adjusted, and the focus is adjusted.

The operating mode change switch 228 is an example of an operating device for changing the operating mode of the arm 204 in the imaging device 206. By performing an operation on the operating mode change switch 228, the operating mode of the arm 204 is changed. Examples of operating modes of the arm 204 include a locked mode and a free mode, as described above.

One example of an operation with respect to the operating mode change switch 228 is an operation of pressing the operating mode change switch 228. For example, the operating mode of the arm 204 becomes the free mode while the surgeon is pressing the operating mode change switch 228, and the operating mode of the arm 204 becomes the locked mode when the surgeon is not pressing the operating mode change switch 228.

In addition, the imaging device 206 is provided with, for example, an anti-slip member 230 and a projecting member 232 in order to further raise operability, convenience, and the like when an operator who performs operations on various operation devices performs an operation.

The anti-slip member 230 is a member provided to prevent slipping of an operating body such as a hand when, for example, the operator performs an operation on the barrel member 222 with the operating body. The anti-slip member 230 is formed with a material having a large coefficient of friction, for example, and has a slip-resistant structure due to unevenness or the like.

The projecting member 232 is member provided to prevent an operating body such as a hand blocking the field of view of the optical system 220a when the operator performs an operation on the barrel member 222 with the operating body, or to prevent a cover glass (not illustrated) from becoming dirty due to the cover glass being contacted by the operating body when an operation is performed with the operating body.

Note that the position and shape in which each of the anti-slip member 230 and the projecting member 232 is provided obviously are not limited to the example illustrated in FIG. 3. In addition, the imaging device 206 does not have to be provided with one or both of the anti-slip member 230 and the projecting member 232.

The image signal (image data) generated by imaging in the imaging device 206 is subjected to image processing in a processor provided in the medical observation apparatus 200, for example. Examples of image processing according to the present embodiment include one or multiple processes from among various processes such as gamma correction, white balance adjustment, image enlargement or reduction related to the electronic zoom function, and pixel interpolation, for example.

Note that in the case in which the medical observation system according to the present embodiment includes a medical control apparatus (not illustrated) that controls various operations in the medical observation apparatus 200, the image processing according to the present embodiment may also be performed in the medical control apparatus (not illustrated).

For example, the medical observation apparatus 200 transmits a display control signal and the image signal subjected to various image processing such as gamma correction to the medical observation apparatus 100.

By transmitting the display control signal and the image signal to the medical observation apparatus 100, on the display screen of the display device (described later) provided in the medical observation apparatus 100, a first medical captured image in which the observation target is imaged (for example, a captured image in which the operating site is imaged) may be displayed enlarged or reduced at a desired magnification by one or both of the optical zoom function and the electronic zoom function.

The medical observation apparatus 200 illustrated in FIG. 2 includes the hardware configuration illustrated with reference to FIGS. 2 and 3, for example.

Note that the hardware configuration of the medical observation apparatus according to the present embodiment is not limited to the configuration illustrated with reference to FIGS. 2 and 3.

For example, the medical observation apparatus according to the present embodiment may also be a configuration not provided with the base 202, in which the arm 204 is directly attached to the ceiling, a wall, or the like of the operating room or the like. For example, in the case in which the arm 204 is attached to the ceiling, the medical observation apparatus according to the present embodiment becomes a configuration in which the arm 204 hangs down from the ceiling.

Also, although FIG. 2 illustrates an example in which the arm 204 is configured so that six degrees of freedom are realized with respect to the driving of the imaging device 206, the configuration of the arm 204 is not limited to a configuration whereby the degrees of freedom with respect to the driving of the imaging device 206 become six degrees of freedom. For example, it is sufficient to configure the arm 204 so that the imaging device 206 can move appropriately in accordance with the application, and factors such as the number and arrangement of joint sections and links, and the directions of the drive shafts of the joint sections can be set appropriately so that the arm 204 has the desired degrees of freedom.

Also, although FIGS. 2 and 3 illustrate an example in which various types of operating devices for controlling the operation of the imaging device 206 are provided on the imaging device 206, some or all of the operating devices illustrated in FIGS. 2 and 3 may also not be provided on the imaging device 206. To give one example, the various types of operating devices for controlling the operation of the imaging device 206 may also be provided in another part other than the imaging device 206 included in the medical observation apparatus 200. Also, to give another example, the various types of operating devices for controlling the operation of the imaging device 206 may also be external operating devices, such as a footswitch FS or a remote controller.

Additionally, the imaging device 206 may also have a configuration enabling switching among multiple observation modes. Observation modes according to the present embodiment may include, for example, an observation mode that executes imaging with natural light, an observation mode that executes imaging with special light, an observation mode that executes imaging by utilizing an image-enhancing observation technology such as narrow-band imaging (NBI), and the like. Special light according to the present embodiment refers to light in a specific wavelength band, such as light in the fluorescent wavelength band of fluorescent observation using 5-Aminolevulinic acid (5-ALA).

One example of the configuration of the imaging device 206 enabling switching among multiple observation modes is a "configuration provided with a filter that allows light of a specific wavelength band to pass through while not allowing light of other wavelength bands to pass through, and a movement mechanism that selectively disposes the filter on the optical path", for example. The specific wavelength band that the filter according to the present embodiment allows to pass through may be, for example, the wavelength band of near-infrared rays (for example, the wavelength band from approximately 0.7 [micrometers] to 2.5 [micrometers]), the fluorescent wavelength band for fluorescent observation using 5-ALA (for example, the wavelength band from approximately 0.6 [micrometers] to 0.65 [micrometers]), the fluorescent wavelength band of indocyanine green (ICG) (for example, the wavelength band from approximately 0.82 [micrometers] to 0.85 [micrometers]), or the like.

Note that the imaging device 206 may also be provided with multiple filters that allow different wavelength bands to pass through. Also, although the above illustrates an example in which imaging is executed with the light of a specific wavelength band by disposing a filter on the optical path, the configuration of the imaging device 206 for executing imaging with the light of a specific wavelength band obviously is not limited to the example illustrated above.

[1-2] Medical Observation Apparatus According to Present Embodiment

Next, the medical observation apparatus 100 including both the function of an optical magnifying glass and the function of a surgical microscope will be described. As described with reference to FIG. 1, the medical observation apparatus 100 is a wearable medical observation apparatus used by being worn directly on the head of the user or a wearable medical observation apparatus used by being worn indirectly on the head of the user.

[1-2-1] Medical Observation Apparatus According to First Embodiment

Figure 4:
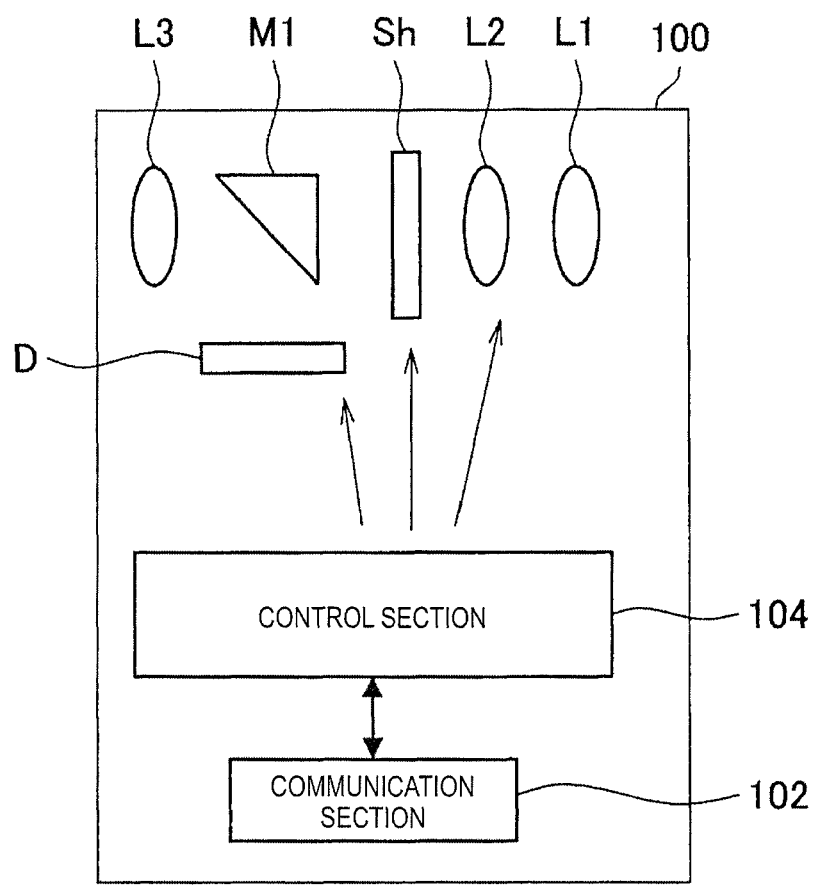
FIG. 4 is an explanatory diagram illustrating one example of the configuration of a medical observation apparatus according to the first embodiment.

FIG. 4 is an explanatory diagram illustrating one example of the configuration of the medical observation apparatus 100 according to the first embodiment. For example, the medical observation apparatus 100 runs on electric power supplied from an internal power source such as a battery provided in the medical observation apparatus 100, on electric power supplied from a connected external power source, or the like (the same applies to the medical observation apparatus 100 according to other embodiments described later).

As illustrated in FIG. 4, the medical observation apparatus 100 is provided with a pair of optical systems, namely a pair of objective lenses L1, a pair of magnifying lenses L2, and a pair of eyepiece lenses L3, in correspondence with each of the two eyes of the user who wears the medical observation apparatus 100. The pairs of objective lenses L1, magnifying lenses L2, and eyepiece lenses L3 are a configuration enabling optical observation in which the user observes the observation target directly through the optical systems, and are one example of a configuration enabling the first observation. In the medical observation apparatus 100 according to the first embodiment, the pairs of objective lenses L1, magnifying lenses L2, and eyepiece lenses L3 fulfill the role of a first observation section.

In the pair of optical systems each including the objective lens L1, the magnification is adjusted by changing the position of the magnifying lens L2. The position of the magnifying lens L2 may be changed by an actuator (not illustrated), or may be changed manually by the user of the medical observation apparatus 100.

In other words, the pair of optical systems each including the objective lens L1 is one example of a configuration made to function as an optical magnifying glass for observing at a low magnification compared to a surgical microscope. By including the pair of optical systems, the user wearing the medical observation apparatus 100 is able to observe the observation target stereoscopically at a relatively low magnification.

Additionally, the medical observation apparatus 100 is provided with a pair of electronic shutters Sh, a pair of half-mirrors M1, and a pair of display devices D, in correspondence with each of the two eyes of the user who wears the medical observation apparatus 100.

Each of the electronic shutters Sh is provided on the optical path of the pair of optical systems, and by opening or closing the electronic shutter Sh, the optical path is selectively blocked. The opening and closing of the electronic shutters Sh is controlled by a control section 104, for example.

By putting the electronic shutters Sh in an open state, the medical observation apparatus 100 enters a state in which the first observation is available. Also, by putting the electronic shutters Sh in a closed state, the medical observation apparatus 100 enters a state in which the first observation is unavailable. In other words, in the medical observation apparatus 100, by opening and closing each of the pair of electronic shutters Sh, it is possible to switch between the state in which the first observation is available and the state in which the first observation is unavailable.

The display devices D are provided at "positions where the user wearing the medical observation apparatus 100 is able to see an image displayed on the display screens of the display devices D through the half-mirrors M1 and the objective lenses L3". The display devices D may be, for example, liquid crystal displays, organic electro-luminescence (EL) displays, or the like.

On the display screens of the display devices D, various images such as the first medical observation image and an image related to a user interface (UI) may be displayed, for example. The display of images such as the first medical observation image on the display devices D is controlled by the control section 104, for example.

By causing a state in which the first medical observation image is displayed on the display devices D, the medical observation apparatus 100 enters a state in which the second observation is available. In other words, the display devices D correspond to a configuration enabling the second observation, and fulfill the role of a second observation section. Note that the configuration in which the second observation is available may also be interpreted as including the half-mirrors M1 and the eyepiece lenses L3.

Also, by causing a state in which the first medical observation image is not displayed on the display devices D, the medical observation apparatus 100 enters a state in which the second observation is not available.

In other words, in the medical observation apparatus 100, by displaying or not displaying the first medical observation image on the display devices D, it is possible to switch between the state in which the second observation is available and the state in which the second observation is unavailable.

In addition, the medical observation apparatus 100 is provided with a communication section 102 and a control section 104.

The communication section 102 is a communication device provided in the medical observation apparatus 100, and fulfills a role of communicating in a wireless or wired manner with an external apparatus such as the medical observation apparatus 200. For example, by communicating with the medical observation apparatus 200 through the communication section 102, the medical observation apparatus 100 acquires the first medical observation image from the medical observation apparatus 200. Also, for example, by communicating with an external apparatus such as the navigation apparatus described above through the communication section 102, the medical observation apparatus 100 is able to acquire information indicating the position of the first observation from the external apparatus. The communication device included in the communication section 102 may be, for example, an IEEE 802.15.1 port and transmitting-receiving circuit (wireless communication), an IEEE 802.11 port and transmitting-receiving circuit (wireless communication), a communication antenna and an RF circuit (wireless communication), a LAN terminal and a transmitting-receiving circuit (wired communication), or the like. Communication in the communication section 102 is controlled by the control section 104, for example.

The control section 104 includes one or multiple processors including a computational circuit such as an MPU, for example, and fulfills the role of controlling the medical observation apparatus 100 overall.

Also, the control section 104 controls the observation state of the observation target in the medical observation apparatus 100.

More specifically, for example, the control section 104 controls the switching between the state in which the first observation is available and the state in which the second observation is available.

As described above, in the medical observation apparatus 100, by opening and closing the electronic shutters Sh, it is possible to switch between the state in which the first observation is available and the state in which the first observation is unavailable. Also, in the medical observation apparatus 100, by displaying or not displaying the first medical observation image on the display devices D, it is possible to switch between the state in which the second observation is available and the state in which the second observation is unavailable.

As illustrated below, for example, by controlling each of the opening and closing of the electronic shutters Sh and the display of the display devices D, the control section 104 controls the switching between the state in which the first observation is available and the state in which the second observation is available.

State in which first observation is available (state of observation by optical magnifying glass): electronic shutters Sh=open state, display devices D=turned-off state State in which second observation is available (state of observation by microscope): electronic shutters Sh=closed state, display devices D=state of displaying first medical observation image In other words, by putting the electronic shutters Sh in the open state and causing the display devices D not to display an image, the control section 104 realizes "the state in which the first observation is available and also in which the second observation is unavailable". Also, by putting the electronic shutters Sh in the closed state and causing the first medical observation image to be displayed on the display devices D, the control section 104 realizes "the state in which the second observation is available and also in which the first observation is unavailable".

The control section 104 controls the switching between the state in which the first observation is available and the state in which the second observation is available as above on the basis of a predetermined operation, for example.

The predetermined operation according to control of observation state of the observation target may be any or all of an operation with respect to an operating device (not illustrated) provided in the medical observation apparatus 100, an operation with respect to an external operating device such as a remote controller or the footswitch FS, a gesture-based operation (an operation performed by the motion of any recognition target for which a gesture is recognizable, such as line of sight or a hand), or a speech-based operation, for example.

The medical observation apparatus 100 determines that the predetermined operation has been performed in "the case in which an operation signal corresponding to an operation performed on any of various types of operating devices is detected", "the case in which a specific motion is detected from the motion of any recognition target, such as line of sight or a hand, obtained by executing a gesture recognition process of any type", or "the case in which specific speech is detected from a speech recognition result obtained by executing a speech recognition process of any type", for example. The motion data used to detect the specific motion above or character string data (or speech data) used to detect the specific speech above is stored in a recording medium (not illustrated) that functions as a storage section (not illustrated), for example. The above gesture recognition process of any type and the above speech recognition process of any type may be executed by the medical observation apparatus 100 or by an apparatus external to the medical observation apparatus 100, such as a medical control apparatus (not illustrated).

Note that the control of the observation state of the observation target in the control section 104 is not limited to the examples illustrated above.

For example, the control section 104 may also control the function of an optical magnifying glass in the state in which the first observation is available. The control of the function of an optical magnifying glass may be the control of any function made available by the optical magnifying glass, such as control of the magnification by control of the position of the magnifying lenses L2 as described above, or control of the illumination intensity by control of an illuminating device (not illustrated) related to the first observation, for example.

In addition, the control section 104 may also cause the display devices D to display an image while the electronic shutters Sh are in the open state, for example. One example of causing the display devices D to display an image while the electronic shutters Sh are in the open state is the "example of causing the display devices D to display an annotation image of any type with respect to the observation target being observed by the first observation".

As illustrated in FIG. 4, for example, the medical observation apparatus 100 according to the first embodiment is provided with a configuration enabling the first observation and a configuration enabling the second observation of the observation target, in which the observation state of the observation target is controlled by control in the control section 104.

Herein, by providing the configuration enabling the first observation of the observation target, the function of an optical magnifying glass is realized in the medical observation apparatus 100. Also, by providing the configuration enabling the second observation, the function of a surgical microscope is realized in the medical observation apparatus 100.

Consequently, with the configuration according to the first embodiment illustrated in FIG. 4, for example, a medical observation apparatus including both the function of an optical magnifying glass and the function of a surgical microscope is realized.

Note that the configuration of the medical observation apparatus 100 according to the first embodiment is not limited to the example illustrated in FIG. 4.

For example, in the case of communicating with an external apparatus via an external communication device having a function and configuration similar to the communication section 102, the medical observation apparatus 100 according to the first embodiment may also not be provided with the communication section 102.

[1-2-2] Medical Observation Apparatus According to Second Embodiment

Figure 5:
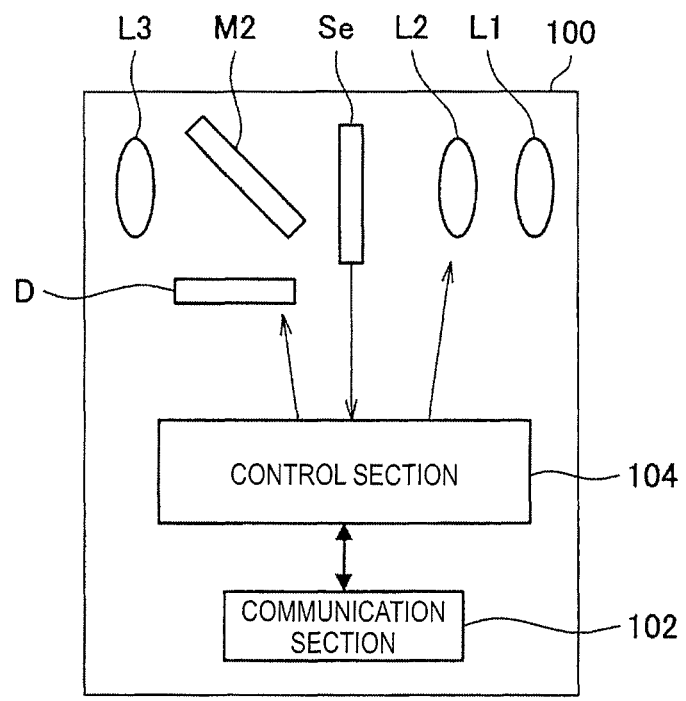
FIG. 5 is an explanatory diagram illustrating one example of the configuration of a medical observation apparatus according to the second embodiment.

FIG. 5 is an explanatory diagram illustrating one example of the configuration of the medical observation apparatus 100 according to the second embodiment.

A comparison between the configuration of the medical observation apparatus 100 according to the first embodiment illustrated in FIG. 4 and the configuration of the medical observation apparatus 100 according to the second embodiment illustrated in FIG. 5 reveals that the medical observation apparatus 100 according to the second embodiment is different by being provided with image sensors Se instead of the electronic shutters Sh and also being provided with mirrors M2 instead of the half-mirrors M1. In the following, the differences from the medical observation apparatus 100 according to the first embodiment will be described, whereas description will be omitted for the points that are similar.

Each of the image sensors Se is provided on the optical path of the pair of optical systems, and an image of optical observation is captured by the image sensors Se. The image sensors Se correspond to one example of the "second imaging device" that images the observation target through the optical system. Also, the image capturing the images of optical observation by the image sensors Se corresponds to one example of the "second medical observation image". The image sensors Se may be, for example, an image sensor using multiple imaging elements such as CMOS and CCD elements. The pairs of objective lenses L1, magnifying lenses L2, image sensors Se, and display devices D are a configuration enabling observation in which the user observes the observation target by the second medical observation image, and are another example of a configuration enabling the first observation. In the medical observation apparatus 100 according to the second embodiment, the pairs of objective lenses L1, magnifying lenses L2, image sensors Se, and display devices D fulfill the role of the first observation section. Note that the configuration in which the first observation is available according to the second embodiment may also be interpreted as including the mirrors M2 and the eyepiece lenses L3.

The image sensors Se transmit an image signal (an analog signal or a digital signal) expressing the second medical observation image to the control section 104.

The control section 104 according to the second embodiment controls the display on the display devices D and thereby controls the observation state of the observation target.

At this point, by causing a state in which the second medical observation image is displayed on the display devices D, the medical observation apparatus 100 enters a state in which observation of the second medical observation image is available, or in other words, a state in which the first observation is available. Also, by causing a state in which the first medical observation image is displayed on the display devices D, the medical observation apparatus 100 enters a state in which the second observation is available.

Therefore, by controlling the display of the second medical observation image on the display devices D, the control section 104 is able to switch between the state in which the first observation is available and the state in which the first observation is unavailable. Also, by controlling the display of the first medical observation image on the display devices D, the control section 104 is able to switch between the state in which the second observation is available and the state in which the second observation is unavailable.

More specifically, by causing the display devices D to display the second medical observation image, the control section 104 realizes "the state in which the first observation is available and also in which the second observation is unavailable". Also, by causing the display devices D to display the first medical observation image, the control section 104 realizes "the state in which the second observation is available and also in which the first observation is unavailable".

For example, by having the control section 104 control the display on the display devices D as above, in the medical observation apparatus 100 according to the second embodiment, switching between the state in which the first observation is available and the state in which the second observation is available may be realized. Similarly to the control section 104 according to the first embodiment, the control section 104 controls the switching between the state in which the first observation is available and the state in which the second observation is available on the basis of a predetermined operation.

Note that processes in the control section 104 according to the second embodiment are not limited to the example illustrated above.

For example, the control section 104 may also cause image data expressing the second medical observation image to be recorded to a recording medium (not illustrated) that functions as a storage section (not illustrated) or a recording medium external to the medical observation apparatus 100. Additionally, the control section 104 may also cause image data expressing the second medical observation image to be transmitted to an external apparatus such as the medical observation apparatus 200.

The medical observation apparatus 100 according to the second embodiment has a configuration basically similar to the medical observation apparatus 100 according to the first embodiment, and by controlling the display on the display devices D in the control section 104, the observation state of the observation target is controlled.

Consequently, even with the configuration according to the second embodiment illustrated in FIG. 5, for example, a medical observation apparatus including both the function of an optical magnifying glass and the function of a surgical microscope is realized.

Note that the configuration of the medical observation apparatus 100 according to the second embodiment is not limited to the example illustrated above.

For example, the medical observation apparatus 100 according to the second embodiment may also have a configuration capable of switching between multiple observation modes. The observation modes in the medical observation apparatus 100 may be, for example, an observation mode that captures an image under natural light and an observation mode that captures an image under special light.

One example of a configuration of the medical observation apparatus 100 capable of switching between multiple observation modes is a "configuration provided with a filter that transmits light of a specific wavelength band and does not transmit light of other wavelength bands, and a movement mechanism that selectively positions the filter on the optical path between the image sensors Se and the magnifying lenses L2", for example. The placement of the filter by the movement mechanism is controlled by the control section 104, for example.

By having the medical observation apparatus 100 according to the second embodiment have a configuration capable of switching between multiple observation modes, special light observation over a wider field of view than a surgical microscope through the use of the function of an optical magnifying glass becomes possible, for example.

[1-2-3] Medical Observation Apparatus According to Third Embodiment

The medical observation apparatus 100 including both the function of an optical magnifying glass and the function of a surgical microscope is not limited to the medical observation apparatus 100 according to the first embodiment described with reference to FIG. 4 or the medical observation apparatus 100 according to the second embodiment described with reference to FIG. 5.

For example, the medical observation apparatus 100 according to the third embodiment may also be provided with a device for detecting the position of the first observation in addition to the configuration of the medical observation apparatus 100 according to the first embodiment or the medical observation apparatus 100 according to the second embodiment. The position of the first observation is detected by an external apparatus, for example. Note that the position of the first observation may also be detected by another method, such as detection by performing any type of image recognition process on the second medical observation image.

The external apparatus that detects the position of the first observation may be the navigation apparatus described above, for example. In the case in which the position of the first observation is detected by the external apparatus, the medical observation apparatus 100 acquires information indicating the position of the first observation by communication through the communication section 102, for example. Additionally, the device for detecting the position of the first observation may be the position-detecting probe described above, for example. The position-detecting probe has a configuration corresponding to the position-detecting method, such as a marker that reflects light of a specific wavelength such as infrared light or a light-emitting device that emits light of a specific wavelength such as infrared light, for example.

As described above, the navigation apparatus may include a function of transmitting position information indicating the detected spatial position of the position-detecting probe to an external apparatus such as the electronic imaging medical observation apparatus 200. Also, by transmitting positional information to the medical observation apparatus 200 for example, in the medical observation apparatus 200, it is possible to control the arm 204 such that an image is captured from a position corresponding to the position indicated by the position information.

Therefore, by using the medical observation apparatus 100 according to the third embodiment provided with a device for detecting the position of the first observation, it is possible to "align the observation field of view of the first observation realized by the function of an optical magnifying glass and the observation field of view of the second observation in the medical observation apparatus 100" more easily.

Also, as above, in the case of causing the observation field of view of the first observation realized by the function of an optical magnifying glass and the observation field of view of the second observation in the medical observation apparatus 100 to work together, the medical observation apparatus 100 according to the third embodiment may also cause a state of alignment with the observation field of view of the second observation to be displayed inside the observation field of view of the first observation. "Causing a state of alignment with the observation field of view of the second observation to be displayed inside the observation field of view of the first observation" corresponds to "in the state in which the first observation is available, presenting the position of the observation field of view of the second observation inside the observation field of view of the first observation". In the medical observation apparatus 100 according to the third embodiment, the control section 104 causes the state of alignment to be displayed on a display screen D on the basis of information acquired from the navigation apparatus (such as position information corresponding to the medical observation apparatus 100 and position information corresponding to the medical observation apparatus 200, for example). One example of the case of causing the state of alignment to be displayed on the display screen D is similar to an example illustrated in the fourth embodiment described later, and therefore will be described later.

Also, the medical observation apparatus 100 according to the third embodiment is provided with the configuration of the medical observation apparatus 100 according to the first embodiment or the medical observation apparatus 100 according to the second embodiment. Therefore, the medical observation apparatus 100 according to the third embodiment exhibits advantageous effects similar to the medical observation apparatus 100 according to the first embodiment or the medical observation apparatus 100 according to the second embodiment.

[1-2-4] Medical Observation Apparatus According to Fourth Embodiment

The medical observation apparatus 100 according to the first embodiment to the third embodiment described above illustrate examples in which the control section 104 switches between the state in which the first observation is available and the state in which the second observation is available. However, the configuration of the medical observation apparatus 100 according to the present embodiment is not limited to a "configuration in which the state in which the first observation is available and the state in which the second observation is available are switched under control by the control section 104".

For example, the medical observation apparatus 100 according to the present embodiment may be provided with each of a configuration enabling the first observation and a configuration enabling the second observation of the observation target, and whether to perform the first observation or the second observation may be switched according to the line of sight of the user wearing the medical observation apparatus 100.

Figure 6:
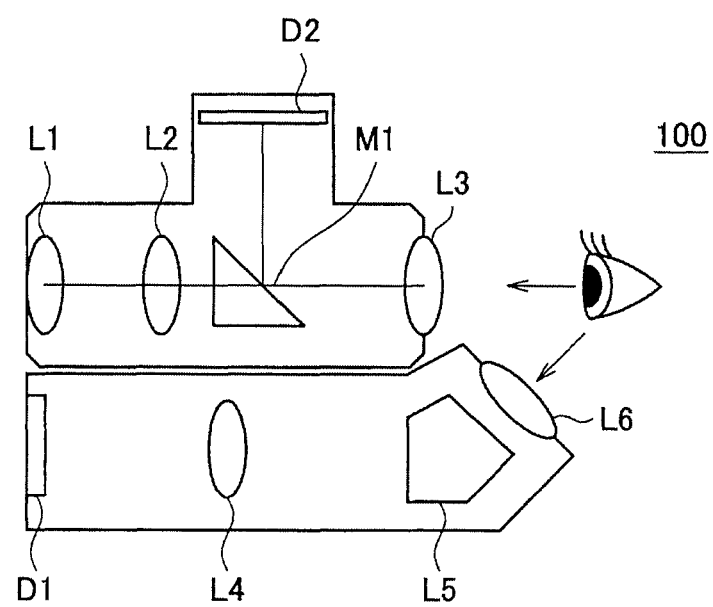
FIG. 6 is an explanatory diagram illustrating one example of the configuration of a medical observation apparatus according to the fourth embodiment.

FIG. 6 is an explanatory diagram illustrating one example of the configuration of the medical observation apparatus 100 according to the fourth embodiment. FIG. 6 illustrates only the configuration corresponding to one eye of the user who wears the medical observation apparatus 100. The configuration illustrated in FIG. 6 is provided as a pair in correspondence with each of both eyes of the user who wears the medical observation apparatus 100.

Note that, although not illustrated in FIG. 6, the medical observation apparatus 100 according to the fourth embodiment is provided with the control section 104, similarly to the medical observation apparatus 100 according to the first embodiment to the third embodiment described above. In addition, the medical observation apparatus 100 according to the fourth embodiment may also be provided with the communication section 102, similarly to the medical observation apparatus 100 according to the first embodiment to the third embodiment described above.

First, one example of the configuration enabling the first observation of the observation target (one example of the configuration that fulfills the role of the first observation section) according to the fourth embodiment will be described. The medical observation apparatus 100 is provided with the objective lens L1, the magnifying lens L2, and the eyepiece lens L3. Additionally, the medical observation apparatus 100 is provided with a half-mirror M1 between the magnifying lens L2 and the eyepiece lens L3, and a display device D2 at a position where the display of the display screen is visible via the half-mirror M1 and the eyepiece lens L3. The display device D2 may be, for example, a liquid crystal display or an organic EL display.

Various images may be displayed on the display screen of the display device D2, such as an annotation image of any type corresponding to the observation target being observed by the first observation and an image related to a UI, for example. The display of images such as an annotation image on the display device D2 is controlled by the control section 104.

Next, one example of the configuration enabling the second observation (one example of the configuration that fulfills the role of the second observation section) according to the fourth embodiment will be described. The medical observation apparatus 100 is provided with a display device D1, an image-forming lens L4, a prism L5, and an eyepiece lens L6. The user who wears the medical observation apparatus 100 recognizes the displayed content on the display screen of the display device D1 via the image-forming lens L4, the prism L5, and the eyepiece lens L6. The display device D1 may be, for example, a liquid crystal display or an organic EL display.

Various images may be displayed on the display screen of the display device D1, such as the first medical observation image and an image related to a UI, for example. The display of images such as the first medical observation image on the display device D1 is controlled by the control section 104, for example.

Figure 7:
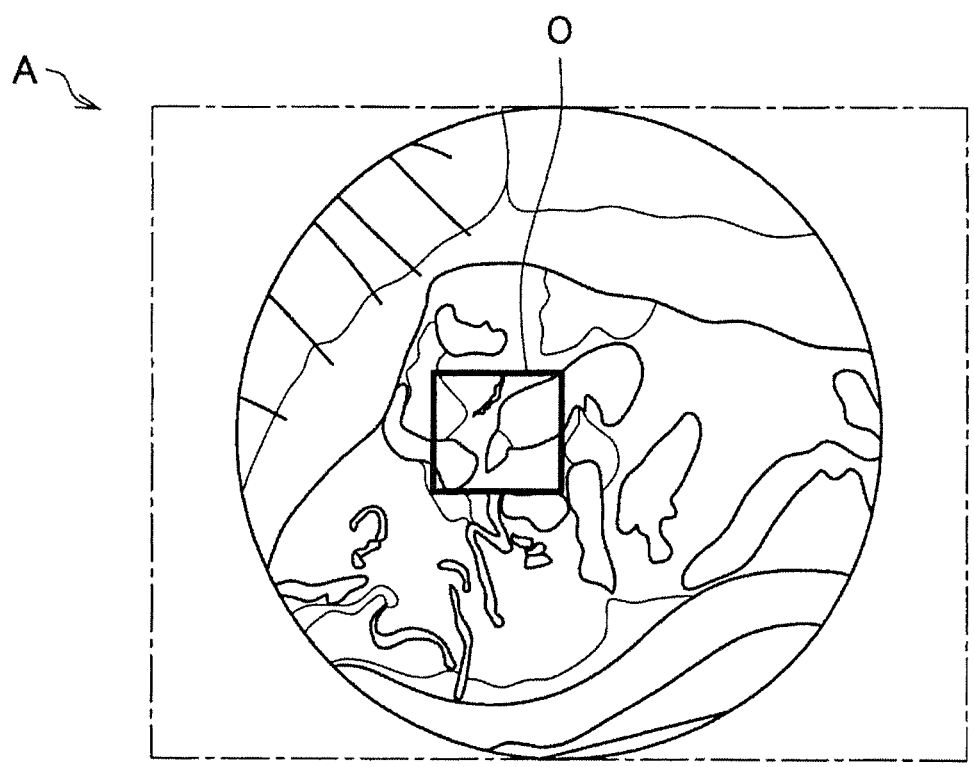
FIG. 7 is an explanatory diagram for explaining one example of a medical observation apparatus according to the fourth embodiment.
Figure 7:
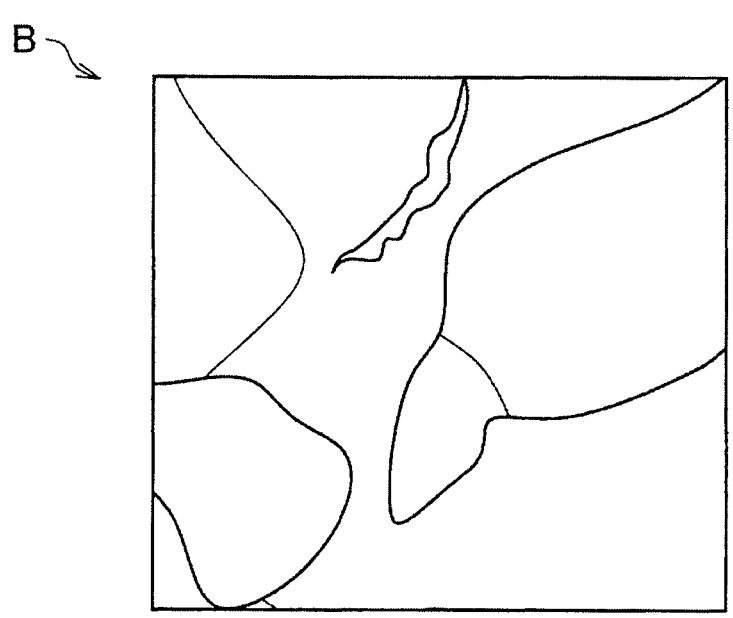

FIG. 7 is an explanatory diagram for explaining one example of the medical observation apparatus 100 according to the fourth embodiment. A of FIG. 7 illustrates one example of an image of optical observation that the user wearing the medical observation apparatus 100 sees via the eyepiece lenses L3. Also, B of FIG. 7 illustrates one example of the first medical observation image that the user wearing the medical observation apparatus 100 sees via the eyepiece lenses L6.

By moving one's line of sight, the user wearing the medical observation apparatus 100 is able to switch to the image of optical observation as illustrated in A of FIG. 7 or to the first medical observation image as illustrated in B of FIG. 7.

The object indicated by the sign O illustrated in A of FIG. 7 indicates the range of the observation field of view of the second observation. The control section 104 causes the object O to be displayed on the display screen of the display device D2 on the basis of information acquired from the navigation apparatus. As a result, the user wearing the medical observation apparatus 100 is able to recognize the range of the observation field of view of the second observation by the object O. The display example illustrated in A of FIG. 7 corresponds to one example of a case of causing a state of alignment with the observation field of view of the second observation to be displayed inside the observation field of view of the first observation, or in other words, one example of a case of, in the state in which the first observation is available, presenting the position of the observation field of view of the second observation inside the observation field of view of the first observation.

Note that an example of the display on the display screen on the display device D2 obviously is not limited to the example illustrated in A of FIG. 7, and an example of the display on the display screen on the display device D1 obviously is not limited to the example illustrated in B of FIG. 7.

[2] Example of Advantageous Effects Exhibited by Use of Medical Observation Apparatus According to Present Embodiment By using the medical observation apparatus 100 according to the present embodiment, the advantageous effects indicated below are exhibited, for example. Note that the advantageous effects exhibited by using the medical observation apparatus 100 according to the present embodiment obviously are not limited to the examples indicated below.

In the medical observation apparatus 100 according to the first embodiment, it is possible to switch instantly between magnifying glass observation at a relatively low magnification and surgical microscope observation at a medium-high magnification. Therefore, by using the medical observation apparatus 100 according to the first embodiment, a user such as a surgeon is able to select an observation method without stress between the case of wanting to work quickly with a relatively wide field of view when cardiac surgery or the like is performed, and the case of wanting to carry out delicate procedures at a high magnification.

In the medical observation apparatus 100 according to the second embodiment, by converting magnifying glass observation to an electronic image, it becomes possible to support special light observation while additionally recording and sharing the image from the magnifying glass observation, thereby improving the medical efficiency of the team.

In the medical observation apparatus 100 according to the third embodiment, since it is possible to automatically track the observation position of the magnifying glass and the observation position of the surgical microscope, the burden of realigning the observation position is greatly reduced, leading to improved surgical efficiency.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A wearable medical observation apparatus used by being worn on a head of a user, including:
a first observation section having a configuration enabling a first observation of an observation target through an optical system including at least an objective lens;
a second observation section having a configuration enabling a second observation of an observation target by a first medical observation image in which the observation target is imaged by a first imaging device; and
a control section configured to control an observation state of the observation target.

(2) The medical observation apparatus according to (1), in which
the control section controls a switching between a state in which the first observation is available and a state in which the second observation is available.

(3) The medical observation apparatus according to (2), in which
the first observation section has a configuration enabling an optical observation of the observation target by the user, and
the control section
switches between the state in which the first observation is available and a state in which the first observation is unavailable by controlling an opening and a closing of an electronic shutter provided on an optical path of the optical system, and
switches between the state in which the second observation is available and a state in which the second observation is unavailable by controlling a display of the first medical observation image on a display device.

(4) The medical observation apparatus according to (3), in which
the control section
causes a state in which the first observation is available and also in which the second observation is unavailable by putting the electronic shutter in an open state and causing the display device not to display an image, and
causes a state in which the second observation is available and also in which the first observation is unavailable by putting the electronic shutter in a closed state and causing the display device to display the first medical observation image.

(5) The medical observation apparatus according to (2), in which
the first observation section is provided with a second imaging device that images the observation target through the optical system, and has a configuration enabling an observation of a second medical observation image captured by the second imaging device, and
the control section
switches between the state in which the first observation is available and a state in which the first observation is unavailable by controlling a display of the second medical observation image on a display device, and
switches between the state in which the second observation is available and a state in which the second observation is unavailable by controlling a display of the first medical observation image on the display device.

(6) The medical observation apparatus according to (5), in which
the control section
causes a state in which the first observation is available and also in which the second observation is unavailable by causing the display device to display the second medical observation image, and
causes a state in which the second observation is available and also in which the first observation is unavailable by causing the display device to display the first medical observation image.

(7) The medical observation apparatus according to any one of (2) to (6), in which
the control section controls the switching between the state in which the first observation is available and the state in which the second observation is available on the basis of a predetermined operation.

(8) The medical observation apparatus according to any one of (1) to (7), in which
an observation magnification of the observation target in the first observation is lower than an observation magnification of the observation target in the second observation.
(9) The medical observation apparatus according to any one of (1) to (8), in which
the first imaging device is an imaging device external to the medical observation apparatus.
(10) The medical observation apparatus according to any one of (1) to (9), further including:
a communication section configured to communicate with an external apparatus, in which
the first medical observation image is acquired by communication.
(11) The medical observation apparatus according to any one of (1), (2), (5), and (6), in which
when in a state in which the first observation is available, the control section presents a position of an observation field of view of the second observation inside an observation field of view of the first observation.
(12) The medical observation apparatus according to (11), including:
a device configured to detect a position of the first observation.
(13) The medical observation apparatus according to (12), further including:
a communication section configured to communicate with an external apparatus, in which
information indicating the detected position of the first observation is acquired by communication.

What is claimed is:

1. A wearable medical observation apparatus used by being worn on a head of a user, comprising:
an objective lens that provides a first observation of an observation target;
a display to show a second observation of an observation target by a first medical observation image output by a first image sensor, wherein a first observation magnification of the observation target in the first observation is lower than a second observation magnification of the observation target in the second observation; and
circuitry configured to switch between a first state in which only the first observation is available and a second state in which only the second observation is available.

2. The medical observation apparatus according to claim 1, wherein
the objective lens provides an optical observation of the observation target directly to the user, and
the circuitry is configured to
switch between the first state in which the first observation is available and the second state in which the first observation is unavailable by controlling an opening and a closing of an electronic shutter provided on an optical path of the objective lens, and
switch between the second state in which the second observation is available and the first state in which the second observation is unavailable by controlling showing of the first medical observation image on the display.

3. The medical observation apparatus according to claim 2, wherein
the circuitry is configured to:
in the first state, open the electronic shutter and prevent the display from showing an image, and
in the second state, close the electronic shutter and show the first medical observation image on the display.

4. The medical observation apparatus according to claim 1, wherein
a second image sensor that images the observation target through the objective lens and outputs a second medical observation image, and
the circuitry is configured to:
switch between the first state in which the first observation is available and the second state in which the first observation is unavailable by controlling showing of the second medical observation image on the display, and
switch between the second state in which the second observation is available and the first state in which the second observation is unavailable by controlling showing of the first medical observation image on the display.

5. The medical observation apparatus according to claim 4, wherein
the circuitry is configured to:
in the first state in which the first observation is available and also in which the second observation is unavailable, showing the second medical observation image on the display, and
in the second state in which the second observation is available and also in which the first observation is unavailable, showing the first medical observation image on the display.

6. The medical observation apparatus according to claim 1, wherein
the circuitry is configured to control switching between the first state in which the first observation is available and the second state in which the second observation is available on a basis of a predetermined operation.

7. The medical observation apparatus according to claim 1, wherein
the first image sensor is external to the medical observation apparatus.

8. The medical observation apparatus according to claim 1,
wherein the circuitry is configured to communicate with an external apparatus to receive the first medical observation image.

9. The medical observation apparatus according to claim 1, wherein
in the first state in which the first observation is available, the circuitry presents a position of an observation field of view of the second observation inside an observation field of view of the first observation.

10. The medical observation apparatus according to claim 9,
wherein the circuitry is configured to detect a position of the first observation.

11. The medical observation apparatus according to claim 10,
wherein the circuitry is configured to communicate with an external apparatus to receive
the detected position of the first observation.

12. The medical observation apparatus according to claim 1, wherein the second observation is a microscope observation.

13. The medical observation apparatus according to claim 12, wherein the first observation magnification is greater than one.

14. The medical observation apparatus according to claim 1, wherein the observation target is directly viewable through the objective lens.

15. The medical observation apparatus according to claim 1, wherein the observation target is not directly viewable through the objective lens.

16. The medical observation apparatus according to claim 1, wherein
the first medical observation image is displayed on a first display, and
the first observation is by a second medical observation image in which the observation target is imaged by a second image sensor and displayed on a second display.

17. The medical observation apparatus according to claim 16, further comprising a lens for viewing the first medical observation image, wherein the lens is in an optical path of the first display and the objective lens is in an optical path of the second display.

18. The medical observation apparatus according to claim 1, wherein the objective lens is a pair of objective lenses and the first medical observation image is pair of first medical observation images.

19. The medical observation apparatus according to claim 1, further comprising a second lens for viewing the first medical observation image.

* * * * *